United States Patent
Boschetti et al.

(10) Patent No.: US 11,090,259 B2
(45) Date of Patent: Aug. 17, 2021

(54) EFFERVESCENT TABLET

(71) Applicant: ARCORAL PHARMA AS, Hokksund (NO)

(72) Inventors: Silvia Boschetti, Aldeno (IT); Massimiliano Rossi, Trento (IT)

(73) Assignee: EUSA PHARMA (UK) LTD, Hertfordshire (GB)

( * ) Notice: Subject to any disclaimer, the term of this patent is extended or adjusted under 35 U.S.C. 154(b) by 0 days.

(21) Appl. No.: 14/441,901

(22) PCT Filed: Nov. 14, 2013

(86) PCT No.: PCT/EP2013/073857
§ 371 (c)(1),
(2) Date: May 11, 2015

(87) PCT Pub. No.: WO2014/076194
PCT Pub. Date: May 22, 2014

(65) Prior Publication Data
US 2015/0272873 A1    Oct. 1, 2015

Related U.S. Application Data

(60) Provisional application No. 61/727,119, filed on Nov. 16, 2012.

(30) Foreign Application Priority Data

Nov. 16, 2012  (NO) .................................... 20121358

(51) Int. Cl.
*A61K 9/46* (2006.01)
*A61K 9/00* (2006.01)
(Continued)

(52) U.S. Cl.
CPC ............ *A61K 9/0007* (2013.01); *A61K 8/022* (2013.01); *A61K 8/20* (2013.01); *A61K 8/24* (2013.01);
(Continued)

(58) Field of Classification Search
CPC ........ A61K 33/42; A61K 33/06; A61K 33/14; A61K 9/0007; A61K 2800/222; A61K 8/24; A61K 8/19; A61Q 11/00
See application file for complete search history.

(56) References Cited

U.S. PATENT DOCUMENTS 3,651,207 A * 3/1972 Lauster et al. ........... A61K 8/19
424/50
3,903,255 A     9/1975 Gusman et al.
(Continued)

FOREIGN PATENT DOCUMENTS

EP  1837019 A1  9/2007
GB  1269620     4/1972
(Continued)

OTHER PUBLICATIONS

Caphosol TM; Nov. 2008, pp. 1-2; Retrieved from the Internet; URL:http://live.caphosol.com/en/PAT/Home.aspx; retrieved on May 8, 2013.
(Continued)

*Primary Examiner* — Bethany P Barham
*Assistant Examiner* — Barbara S Frazier
(74) *Attorney, Agent, or Firm* — Cantor Colburn LLP

(57) ABSTRACT

The present invention relates to an effervescent tablet, which upon dissolution in water provides a solution useful as a mouth wash or oral rinse for the prevention or treatment of inflammatory processes of the soft tissues of the mouth, throat and oral cavity.

25 Claims, 1 Drawing Sheet

(51) Int. Cl.

| | |
|---|---|
| *A61K 33/14* | (2006.01) |
| *A61K 33/42* | (2006.01) |
| *A61Q 11/00* | (2006.01) |
| *A61K 8/365* | (2006.01) |
| *A61K 8/20* | (2006.01) |
| *A61K 8/02* | (2006.01) |
| *A61K 33/06* | (2006.01) |
| *A61K 8/24* | (2006.01) |
| *A61K 47/02* | (2006.01) |

(52) U.S. Cl.
CPC .............. *A61K 8/365* (2013.01); *A61K 9/006* (2013.01); *A61K 9/0056* (2013.01); *A61K 33/06* (2013.01); *A61K 33/14* (2013.01); *A61K 33/42* (2013.01); *A61K 47/02* (2013.01); *A61Q 11/00* (2013.01); *A61K 2800/222* (2013.01)

(56) References Cited

U.S. PATENT DOCUMENTS

| | | | |
|---|---|---|---|
| 4,127,645 | A | 11/1978 | Witzel et al. |
| 5,817,296 | A | 10/1998 | Winston et al. |
| 5,993,785 | A * | 11/1999 | Johansen ................. A61K 8/19 424/49 |
| 6,387,352 | B1 | 5/2002 | Johansen et al. |
| 2011/0014132 | A1 | 1/2011 | Liu |
| 2011/0086108 | A1 | 4/2011 | Weldon |

FOREIGN PATENT DOCUMENTS

| | | | | |
|---|---|---|---|---|
| GB | 2318977 | A | 5/1998 | |
| WO | 9625914 | | 8/1996 | |
| WO | 9706774 | A1 | 2/1997 | |
| WO | 199813013 | A1 | 4/1998 | |
| WO | 2005011639 | A2 | 2/2005 | |
| WO | WO 2012/002918 | * | 1/2012 | ............... A61K 9/00 |
| WO | 2012156502 | A2 | 11/2012 | |

OTHER PUBLICATIONS

"Caries Prevention Treatment Saves Patients' Teeth After Radiotherapy"; Medical News; JAMA; 234(6); pp. 577-578 (1975).

International Search Report and Written Opinion; International Application No. PCT/EP2013/073857; International Filing Date Nov. 14, 2013; dated Jan. 29, 2014; 12 pages NeutraSol_Powder for Supersaturated Calcium Phosphate Rinse; Invado Pharmaceuticals; Internet Citation 1 page (2011); retrieved from the Internet: URL:http://www.neutrasal.com/uploads/NeutrasalLabeling_april2011_1_.pdf; [retrieved on May 6, 2013].

Papas et al.; "Post-Transplant Complications_A Prospective, Randomized Trial for the Prevention of Mucositis in Patients Undergoing Hematopoietic Stem Cell Transplantation"; Bone Marrow Transplantation; 31; pp. 705-712; (2003).

* cited by examiner

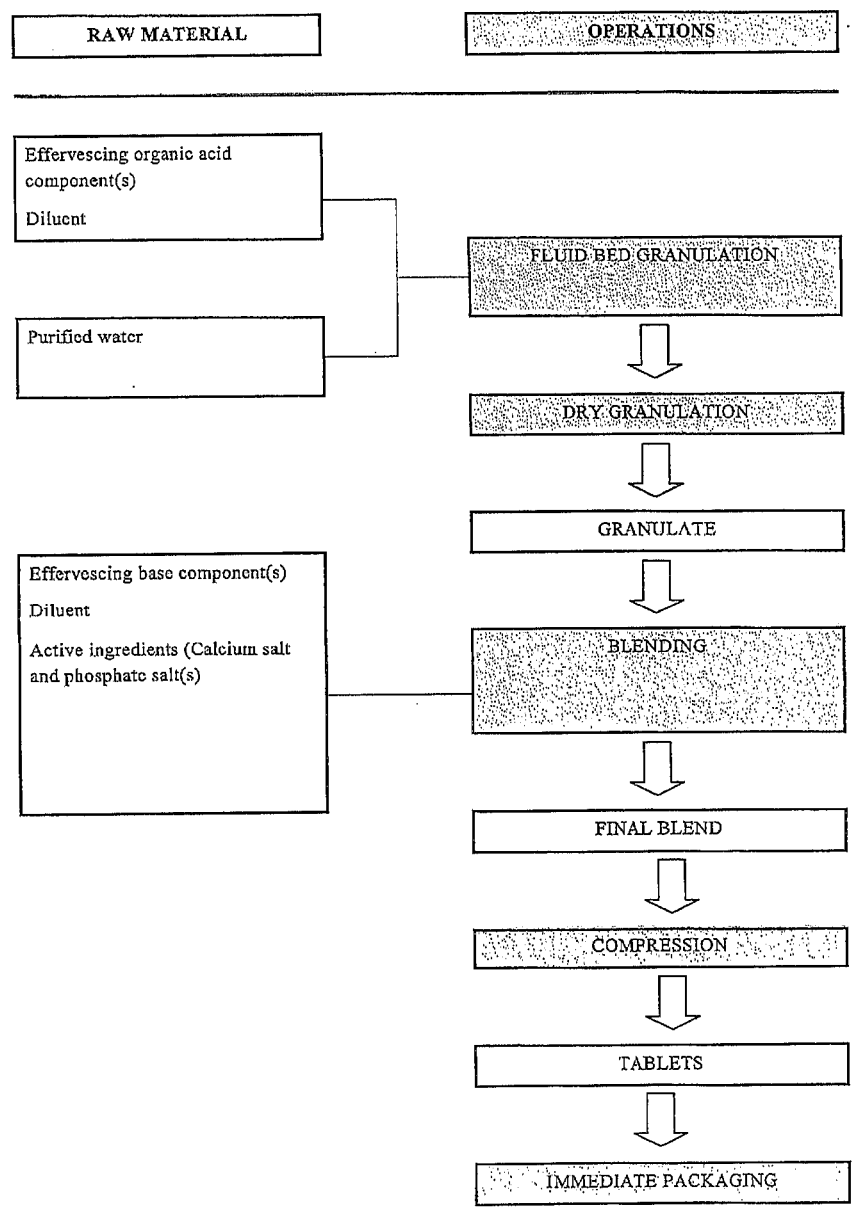

EFFERVESCENT TABLET

CROSS-REFERENCE TO RELATED APPLICATIONS

This application is a 371 of PCT/EP2013/073857 filed on Nov. 14, 2013, which claims the benefit of priority to Norwegian application No: 20121358 filed on Nov. 16, 2012 and U.S. Provisional Application No. 61/727,119 filed on Nov. 16, 2012 under the provisions of 35 U.S.C. § 119 and the International Convention for the protection of Industrial Property, which are incorporated herein by reference in their entirety.

FIELD OF INVENTION

The present invention relates to an effervescent tablet, which upon dissolution in water provides a solution useful as a mouth wash or oral rinse for the prevention or treatment of inflammatory processes of the soft tissues of the mouth, throat and oral cavity. In addition, the present invention relates to a method for preventing or treating inflammatory processes of the soft tissues of the mouth, throat and oral cavity. The present invention furthermore relates to a process for the preparation of effervescent tablets according to the present invention.

BACKGROUND OF THE INVENTION

The use of various medications and different treatment regimes exert side effects resulting in severe injury on the mucous membrane of the oral cavity as well as severe dental injuries. Also, disorders such as AIDS and cancer treatment regimes may result in reduced activity of the immune system which again may result in severe conditions of the oral cavity, such as e.g. mucositis and severe infections.

Cancer patients undergoing bone marrow transplantation are typically administered immune depressing medicinal agent to depress the immune system and thus avoid rejection of the transplanted tissue or cells. Furthermore, cancer patient undergoing cytotoxic drug treatment may often also have reduced immune system due to the cytotoxic effect on the leucocytes. A patient having a depressed immune system is also susceptible to infection resulting in prophylactic treatment with antibiotics. Repetitive and large use of antibiotics, as well as head and neck radiation, may again result in severe dental caries.

Also other patients having reduced immune system activity or being dependent on continuous treatment with antibiotics, immunosuppressive or other medications, such as e.g. AIDS patients, may be affected with the same severe side effects on both hard and soft tissue of the oral cavity. Reduced immune system activity also results in an increased risk of systemic infections due to the increased risk of passage pathogens from the oral cavity to the blood stream.

Chemotherapeutic treatment may also result in discourage eating and malnutrition due to stomatitis, sore throat, change in taste sensation, stomach cramping, nausea, vomiting, diarrhoea etc. The malnutrition condition may further result in undesirable condition affecting both hard and soft tissue in the oral cavity.

Human *salvia* has several important functions in the oral cavity. For example, saliva provides a natural antibacterial protection (due to the fact that saliva provides a tissue coating film). Furthermore, the saliva also has a remineralizing potential due to the lubrication of the mucosa. Several medicinal agents, as well as head and neck radiation, result in dryness of the mount due their adverse effect resulting in reduced salivary production. Mouth dryness as a consequence of adverse effect of medicines may thus lead to various undesired conditions in the oral cavity. Also resulting in a suppressed immune system may lead to various undesired conditions in the oral cavity. Non-limiting examples of medicinal agent which may result in dry mouth are e.g. the anti prostate agent bicalutamide, antidepressive medicaments (citalopram, fluoxetine, paroxetine), carbamazepine (anti epilepticum), lansoprazol (proton pump inhibitor), klozapine (neurolepticum), topiramate (anticonvulsant), olanzapine (anti schizophrenia) etc.

The salivary production may also be severely reduced upon radiation therapy as radiation causes atrophy of the salivary glands in the oral cavity, cf. Medical News, 1975, JAMA, Vol 234, no. 6, pp. 577-578.

An example of another disease affecting the salivary glands leading to reduced salivary production and dry mouth is Sjøgren's syndrome. Thus, patients having Sjøgren's syndrome are also exposed to developing undesirable conditions of the oral cavity, such as mucositis etc.

Many of the side effects and symptoms described above have been treated or avoided by preventive administration of a supersaturated solution of calcium and phosphate. It is known that the treatment with calcium and phosphate mouth rinse may have beneficial effect by reducing mucositis in patients undergoing stem cell transplantation, c.f. Papas et al. (2003), Bone Marrow Transplantation, 00, 1-8. It is furthermore known that the administration of supersaturated calcium phosphate solution, used twice a day after fluoride treatment results in remineralization, c.f. Medical News, 1975, JAMA, vol. 234, no. 6, pp. 577-578.

U.S. Pat. No. 6,387,352 discloses a mouth wash composition supersaturated with respect to calcium and phosphate, suitable for treating patients having dental caries or other conditions in the oral cavity, e.g. as a result of chemotherapy or radiation therapy. More specifically, U.S. Pat. No. 6,387,352 discloses a formulation which is effective for use as a dental rinse or mouth wash, wherein said formulation comprises an aqueous calcium component (calcium stock solution); and separated there from, an aqueous phosphate component (phosphate stock solution).

U.S. Pat. No. 5,993,785 disclose an aqueous solution which are supersaturated with respect to calcium and phosphate(s) and which further comprise a stabilizing agent in an amount sufficient to enable the calcium ions and phosphate ions to remain in supersaturated solution so that it may be used as a dental rinse or mouth wash. U.S. Pat. No. 5,993,785 likewise teach an aqueous calcium component, and separated there from, an aqueous phosphate component.

A composition providing a super saturated solution of calcium and phosphate is at the moment marketed as Caphosol™, cf. http://www.caphosol-us.com/default.asp. Caphosol™ is used to lubricate the mucosa and maintain the integrity of the oral cavity through its mineralizing potential. It is described for inter alia mucositis and dry mouth. Caphosol™ consist of two stock solutions provided in separate, single dosages ampoule, one comprising calcium ions and the other one comprising phosphate ions, which upon mixing yield the super saturated mixture. Upon administration of the super saturated solution of calcium, the calcium component and the phosphate component is mixed by the patient prior to administration.

Thus, patients undergoing chemotherapy or radiation therapy due to cancer, or patients having a depressed or ineffective immune system (patients undergoing bone marrow transplantation, AIDS patients etc), patients having Sjøgren's syndrome, patients with imperfect or non-functioning salivary glands, patients being administrated medicines resulting in dry mouth, patients with high susceptibility to dental caries or who aims at an increased oral health, patients with inflammatory and/or ulcerative lesions in the oral cavity or the susceptibility thereof, etc might benefit from treatment with a supersaturated calcium and phosphate solution.

The challenge of preparing mount washes comprising the necessary amounts of calcium and phosphate ions to provide the beneficial effects of the soft and hard tissue of the oral cavity, is to prepare a solution of calcium ions and phosphate ions which do not results in the precipitation of calcium and phosphate complexes thereof. In U.S. Pat. Nos. 6,387,352 and 5,993,785, super saturated solutions which do not precipitate within the time needed to rinse the oral cavity are disclosed as referred to above. Said super saturated solutions disclosed in U.S. Pat. Nos. 6,387,352 and 5,993,785, as is the fact with Caphosol™, require the patient to mix together two previously prepared and packaged aqueous solutions comprising calcium ions and phosphate ions, respectively. According to one aspect of these prior art mouth rinses two separate aqueous concentrates are provided that requires dilution and then mixing of the to solutions obtained by the patient. According to another aspect of the prior art mouth rinses, the aqueous stock solutions come pre-diluted and separately packaged. Again, the patient will have to mix the pre-diluted solution prior to use.

The prior art mouth rinses discussed above suffer from several disadvantages, however. One such disadvantage is that the starting components used in manufacturing Caphosol™ have to be stirred in large vessels for several hours before they are dissolved properly. Because of this, the preparations disclosed in the prior art must be delivered to the patient as separately packaged, aqueous solutions, which must be mixed together by the patient. This greatly increases the manufacturing, transport, packaging and storage costs of the product. In addition, it is further well known that the use of aqueous solutions as a formulation form necessitates sterilization procedures. In contrast to an aqueous formulation, a solid formulation avoids labour-intensive sterilization or purified water procedures and most often provides for a longer storage life. In addition, the use of such liquid products is inconvenient for the patient, for example requiring the patient to carry large and heavy packaging when travelling.

US2011/0086108 relates to a calcium, phosphate and sodium bicarbonate composition for use as a mouthwash or oral rinse. The solid powder is dissolved in water prior to administration. A powder used to form a supersaturated calcium phosphate rinse according to US2011/0086108 is marketed under the trademark NeutraSal®, http://www.neutrasal.com/uploads/NeutrasalLabeling_april2011_1_.pdf. According to the NeutraSal® package insert, said powder comprises the following ingredients: (active) sodium, phosphate, calcium, chloride and bicarbonate, and silicon diozide (inactive) (http://www.neutrasal.com/uploads/NeutrasalLabeling_april2011_1_.pdf) Although a powder may be more convenient in respect of packaging and storage costs, it's still inconvenient for the patient. E.g., it is a risk for not dissolving the total dose in case some of the powder remains in the dosage packet and thus risking not obtaining the desired supersaturated solution. Furthermore, comparative studies performed by the present inventors show that the dissolution of NeutraSal® yields an opalescent solution comprising insoluble particles.

U.S. Pat. No. 4,127,645 disclose an effervescent tablet useful in inhibiting or reducing dental plaque, and which may include a source of calcium ion to fortify teeth against demineralization. However, the said tablet is not meant for dissolution in water but is to be taken orally as such by the patient. In addition, said composition does not comprise phosphate ions enabling a supersaturated solution of phosphate and calcium ions.

The object of the present invention is to provide a composition useful for providing a mouth rinse having the same therapeutically effect as the prior art product Caphosol™ and as described in U.S. Pat. Nos. 6,387,352 and 5,993,785, but which is provided to the patient in the form of an effervescent tablet to be dissolved in water by the patient prior to administration.

It is further an object of the present invention to overcome the disadvantages connected with the stock solution system and powder systems disclosed in the prior art related to e.g. transport cost, packaging, sterilization, precipitation, storage life etc.

It is furthermore an object of the present invention to overcome the disadvantages in respect of opalescence and presence of particles associated with the dissolution of prior art solid powder when dissolved in water prior to the administration to the patient.

SUMMARY OF THE INVENTION

An effervescent tablet is provided which when dissolved in water provides a supersaturated solution of phosphate and calcium useful as a mouth wash or oral rinse for the prevention or treatment of inflammatory processes of the soft tissues of the mouth, throat and oral cavity.

The effervescent tablet furthermore provides upon dissolution in water a supersaturated solution of phosphate and calcium which remain clear for at least 2 hr, such as e.g. for at least 90 min, for at least 60 min, for at least 30 min, for at least 20 min, for at least 15 min.

According to one aspect of the invention, an effervescent tablet is provided comprising:
  a) a pharmaceutically effective amount of one or more phosphate salts;
  b) a pharmaceutically effective amount of a calcium salt;
  b) one or more effervescing organic acid component;
  c) one or more effervescing base component;
wherein said tablet upon dissolution in water provides a supersaturated solution of calcium and phosphate ions. According to one embodiment, the phosphate salt is a sodium phosphate.

According to another embodiment, the effervescent tablet according to the present invention comprises a pharmaceutically effective amount of dibasic, sodium phosphate and monobasic, sodium phosphate.

According to one embodiment of the present invention, the calcium salt is calcium chloride, more preferably calcium chloride dihydrate. According to another embodiment of the present invention, the effervescing organic acid component is selected from the group consisting of organic mono-, di- and tricarboxylic acids, and oxyacids, salts of organic acids and salts of inorganic acids, and combinations thereof. According to a preferred embodiment of the present invention, the effervescing organic acid is citric acid.

According to another embodiment of the present invention, the one or more effervescing base component is a carbonate salt, such as one or more effervescing base selected from the group consisting of sodium carbonate, magnesium carbonate, sodium hydrogen carbonate, potassium carbonate, potassium hydrogen carbonate, calcium carbonate and magnesium carbonate. According to a preferred embodiment of the present invention, the effervescing base is sodium carbonate and sodium hydrogen carbonate.

According to a further embodiment of the present invention, the pH of the solution obtained when dissolving the effervescent tablet of the invention is about 6.5.

According to yet another embodiment of the invention, the effervescent tablet further comprises one or more additional excipients, such as e.g. one or more carbohydrates selected from the group consisting of polyalcohols, dextrines and saccharides.

According to one embodiment, the effervescent tablet of the present invention comprises one or more one or more polyalcohol selected from the group consisting of sorbitol, mannitol, xylitol, and inositol or the mixture thereof.

According to one embodiment, the effervescent tablet of the present invention comprises one or more saccharides selected from the group consisting of glucose, fructose and sucrose, or the mixture thereof.

According to yet another embodiment, the effervescent tablet according to the invention comprises one or more flavour and/or sweetener, such as e.g. one or more flavour and/or sweetener selected from the group consisting of saccharin, aspartame, and acesulfame.

According to yet another embodiment of the invention, an effervescent tablet is provided, wherein the amount of calcium per tablet is in the range of about 14-24 mg.

According to yet another embodiment of the invention, an effervescent tablet is provided, wherein the amount of phosphate per tablet is in the range of about 28-36 mg.

According to yet another embodiment of the invention, an effervescent tablet is provided, wherein the tablet comprises a molar ratio of $NaH_2PO_4:Na_2HPO_4:CaCl_2 \times 2H_2O$ of about 1:3:6.

According to yet another embodiment of the invention, an effervescent tablet is provided, comprising:
  about 69.1 mg calcium chloride dihydrate;
  about 9.2 mg monobasic sodium phosphate;
  about 31.1 mg dibasic sodium phosphate;
  about 450.0 mg sodium hydrogen carbonate;
  about 50.0 mg sodium carbonate;
  about 238.5 mg citric acid;
  about 225.5 mg maltodextrin; and
  about 26.5 mg sorbitol.

According to yet another embodiment of the invention, an effervescent tablet is provided, comprising:
  about 69.1 mg calcium chloride dihydrate;
  about 9.2 mg monobasic sodium phosphate;
  about 31.1 mg dibasic sodium phosphate;
  about 512.3 mg sodium hydrogen carbonate;
  about 60.6 mg sodium carbonate;
  about 272.7 mg citric acid;
  about 214.6 mg maltodextrin; and
  about 30.3 mg sorbitol.

According to yet another embodiment of the invention, an effervescent tablet is provided, comprising:
  about 69.1 mg calcium chloride dihydrate;
  about 9.2 mg monobasic sodium phosphate;
  about 31.1 mg dibasic sodium phosphate;
  about 1690.5 mg sodium hydrogen carbonate;
  about 200.0 mg sodium carbonate;
  about 900.0 mg citric acid; and
  about 100.0 mg sorbitol.

Another aspect of the invention is a process for the preparation of effervescent tablets according to the invention, comprising the steps of:

a) mixing one or more effervescing organic acid components and a diluent;
b) subjecting the mixture of step a) to granulation;
c) drying the granulate obtained in step b);
d) mixing the granulate of step c) with one or more effervescing base component, a pharmaceutically effective amount of one or more phosphate salt(s), a pharmaceutically effective amount of a calcium salt, and optionally one or more pharmaceutically acceptable excipients; and
e) compressing the mixture of step d) to form tablets.

Yet another aspect of the invention is a process for preventing or treating inflammatory processes of the soft tissues of the mouth, throat and oral cavity, comprising the steps of diluting an effervescent tablet according to the present invention in a suitable amount of water in order to dissolve the tablet, and administer the obtained solution to the patient as a oral rinse.

DESCRIPTION OF DRAWINGS

FIG. 1 shows a flow chart of process for preparing the effervescent tablets of the present invention.

DETAILED DESCRIPTION OF THE INVENTION

The present invention will now be described in more detail with reference to figures and examples. The following description and examples intends to illustrate the present invention, and should in no way be considered limiting. Furthermore, the skilled person will acknowledge that various modifications may be introduced without departing from the scope of the invention. Accordingly, other embodiments of the present invention which are within the abilities of the skilled person are to be understood to be within the scope of the claimed invention.

The present effervescent tablets provides upon dissolution in water a solution useful as a mouth wash or oral rinse useful in the prevention or treatment of inflammatory processes of the soft tissues of the mouth, throat and oral cavity. Upon dissolution of the effervescent tablet of the present invention, the supersaturated solution of calcium and phosphate ions will be obtained. Soluble effervescent tablets providing a supersaturated solution of calcium and phosphate ions have many advantages. For example, it is much more convenient to bring along effervescent tablets when travelling rather than having to bring a long separately packaged, aqueous solutions, which must be mixed together by the patient prior to use.

The term "supersaturated" as used herein is to be understood to mean a solution comprising calcium and phosphate ions, and wherein the concentration of said ions are higher than the concentration of said ions presented in a saturated solution thereof.

An effervescent tablet is a tablet that when added to water, dissolves and results in a solution to be administered to patient, and wherein the dissolution is effectuated due to the production of gas, such as carbon dioxide. The gas is furthermore provided by effervescent excipients contained in the effervescent tablet. The term "effervescent" generally means the escape or production of gas from a liquid or mixture. Thus, the term "effervescent tablet", as used herein, means a tablet that evolve one or more gases under proper conditions, such as upon contact with water, and which results in the complete dissolution of the tablet.

The term "complete dissolution of the tablet" or "completely dissolved effervescent tablet" as used herein it to be understood as the providing a supersaturated solution comprising calcium and phosphate ions which remains clear as long as necessary for the patient to use said solution as a mouth wash and oral rinse. The time for the tablet to be completely dissolved is suitable within a time convenient in respect of patient compliance and patient friendliness. According to one embodiment, the effervescent tablet of the invention is completely dissolved within about 120 sec, such as within about 90 sec, such as within about 60 sec, such as within about 30 sec. Preferably, the effervescent tablet according to the present invention is completely dissolved within 60 sec, more preferably within about 30 sec.

It is furthermore important that the solution obtain upon dissolution of the tablet remains clear and that no precipitation occurs during the time prior to the use of the patent as an oral rinse/mouth wash. According to yet another embodiment, the solution obtained when the effervescent tablet of the invention is completely dissolved in water remains clear for at least 2 hr.

The term "effervescing base component" as used herein means a suitable base which react with "the effervescing organic acid component" resulting in the production of gas, preferably carbon dioxide, whenever the effervescent tablet is added to water. The production of carbon dioxide will furthermore result in effervescence and dissolution of the tablet, and then yield a clear supersaturated solution. The effervescing base component is preferably an alkali metal or alkaline earth metal bicarbonates and hydrogen carbonate component or combinations thereof. A non-limiting list of suitable effervescing base components are sodium carbonate, magnesium carbonate, sodium hydrogen carbonate, potassium carbonate, potassium hydrogen carbonate, calcium carbonate and magnesium carbonate.

The term "effervescing organic acid component" as used herein means a suitable organic acid which react with "the effervescing base component" resulting in the production of gas, preferably carbon dioxide, whenever the effervescent tablet is added to water. The effervescing organic acid may be selected from the group consisting of organic mono-, di- and tricarboxylic acids, and oxyacids, salts of organic acids and salts of inorganic acids, and combinations thereof. For example, monocarboxylic acids such as lactic acid and ascorbic acid may be used. Useful examples of dicarboxylic acids are e.g. tartaric acid, fumaric acid, malic acid, succinic acid, adipic acid and maleic acid. A typical example of a tricarboxylic acid is citric acid. Any salt of the above mentioned organic acids that is pharmaceutically acceptable and which will result in the production of gas upon reaction with the effervescing base component when the tablet are added to water. A non-limiting example of a salt of suitable acids is e.g. the sodium hydrogen phosphate salt.

An effervescent tablet according to the present invention may, in addition to the active ingredients providing a supersaturated solution of calcium ions and phosphate ions, the effervescing organic acid component and the effervescing base component, include additional excipients applicable for preparing effervescent tablets which are well known to the skilled person. For example, the composition may additionally comprise suitable carbohydrates acting as diluters and/or binders, such as polyalcohols, maltodextrin or simple sugar (saccharides). Typical examples of polyalcohols are sorbitol, mannitol, xylitol, and inositol and typical example of sugars are glucose, fructose, and sucrose.

The effervescent tablet of the present invention may also comprise flavours and/or sweeteners providing a nice and/or sweet taste of the solution obtained when dissolving the present effervescent tablet in water. The skilled person is well aware of a range of flavours and sweeteners that may be used to provide a pleasant taste of solutions prepared by dissolution of effervescent tablets. A non-limiting list is e.g. saccharin, aspartame, sucralose, thaumatin, steviosides, neohesperidine and acesulfame.

The effervescent tablets according to the present invention may be prepared using conventional methods for preparing effervescent tablets well known to the skilled person. The skilled person is well known with the known granulation methods used for forming effervescent tablets. Granulation generally includes any processes for size enlargement whereby small particles are gathered together into larger, permanent aggregates to yield a composition having a consistency suitable for tabletting. A granulate may also be mixed with further ingredients, such as excipients and/or active ingredients, to form a composition suitable for tabletting. Granulation may also be performed by spray-drying, such as fluidized bed granulation.

For example, the effervescent tablets of the present invention may be prepared following a manufacturing process as shown in FIG. 1, including conventional fluidized bed granulation, blending and finally compression of tablets according to well-known tabletting processes (c.f. e.g. Lieberman, Pharmaceutical Dosage Form: Tablets, vol. 1, $2^{nd}$ edition, New York, 1989, which disclosure is incorporated by reference in its entirety).

The active ingredient of the present effervescent tablets are the calcium and phosphate ions present in the solution obtained when dissolving said tablets in a suitable amount of water.

The term "pharmaceutically active amount of calcium salt" and "pharmaceutically active amount of phosphate salt" means an amount of said salts which upon dissolution of the effervescent tablet of the present invention results in the providing of a supersaturated solution with respect to calcium ions and phosphate ions.

The calcium and phosphate present in the tablet according to the present invention may be provided using e.g. a pharmaceutically active amount of calcium chloride, preferably calcium chloride dihydrate ($CaCl_2 \times 2H_2O$), and a pharmaceutically active amount of dibasic sodium phosphate ($Na_2HPO_4$) and a pharmaceutically active amount of monobasic sodium phosphate ($NaH_2PO_4$). Preferably, the dibasic sodium phosphate and monobasic sodium phosphate is anhydrous.

According to yet another embodiment, the effervescent tablet of the present invention comprises a molar ratio of monobasic sodium phosphate ($NaH_2PO_4$):dibasic sodium phosphate ($Na_2HPO_4$):calcium chloride dihydrate ($CaCl_2 \times 2H_2O$) is about 1:3:6.

According to yet another embodiment, an effervescent tablet is provided comprising between 14-24 mg/tablet calcium and about 21-35 mg/tablet phosphate. According to another embodiment, an effervescent tablet is provided comprising about 18.5 mg/tablet calcium and about 28 mg/tablet phosphate.

According to another embodiment of the present invention, the concentration of calcium ions provided in the obtained supersaturated solution upon dissolution of the effervescent tablet according to the present invention is in the range of about 2 to about 40 mM, such as e.g. 2 mM to about 21 mM, such as e.g. about 2.5 to about 16 mM. At around neutral pH the concentration of calcium ions is suitably in the range of from 2.5 mM to about 10 mM, such as e.g. 3 mM to 5 mM, for example about 3.87, 4.5 or 5 mM.

According to one embodiment, the calcium ion concentration obtained when diluting a effervescent tablet according to the present invention in 50 ml water is between about 8.0 mM and about 10.0 mM, preferably between about 9.0 mM and 9.5 mM.

According to another embodiment of the present invention, the concentration of phosphate ions provided in the obtained supersaturated solution upon dissolution of the present effervescent tablet is in the range of about 0.5 mM to about 32 mM, such as e.g. 1 mM to about 20 mM, such as e.g. about 1.5 to about 10 mM. At around neutral pH, the concentration of phosphate is suitably in the range of from about 2 to about 8 mM.

According to one embodiment, the phosphate ion concentration obtained when diluting a effervescent tablet according to the present invention in 50 ml water is between about 4.0 mM and about 8.0 mM, preferably between about 5.0 mM and 7.0 mM, preferably between about 5.5 mM and about 6.0 mM.

The pH of the super saturated solution obtained after dissolution of effervescent tablet of the present invention is preferably within the area from about 5 to about 8, more preferably from about 6.0 to about 7.0. According to one embodiment of the present invention, the pH of the super saturated solution obtained upon dissolution of the effervescent tablet is 6.

The effervescent tablet of the present invention may also include compounds facilitating healing of wounds and fissures such as Zink. The effervescent tablet of the present invention may furthermore in addition comprise fluoride in order to prevent caries.

The administration regime of a supersaturated solution obtained by the dissolution of the effervescent tablet according to the present invention may be the same as for supersaturated mouth rinse preparation well known to the skilled person, e.g. such as for Caphosol™ as described in U.S. Pat. Nos. 6,387,352 and 5,993,785 (the entire contents of which are hereby incorporated by reference as if repeated verbatim herein for establishing such regime).

In order to obtain a supersaturated solution useful for the prevention and treatment of inflammatory processes of the soft tissues of the mouth, throat and oral cavity, the effervescent tablet should be dissolved in a suitable amount of water. The term "suitable amount of water" means an amount which upon dissolution of the effervescent tablet of the present invention provides a supersaturated solution comprising calcium and phosphate ions. To prepare the supersaturated solution for ingestion, the effervescent tablet of the present invention are placed in a suitable amount of water, typically 50 ml of water, to provide the dissolution of the tablet, and a clear solution for the patient to use as a mouth wash or oral rinse.

As mentioned above, it is of importance in respect to patient compliance that the solution obtained by dissolution of the effervescent tablet according to the present invention is clear and free of insoluble particles. The dissolution studies provided in the examples below show that the composition according to the present invention results in a supersaturated solution which maintain clear for at least 2 hr. Furthermore, a comparative study (example 7) furthermore show the advantage of the present invention over the prior art powder solution as the latter do not dissolve properly resulting in an opalescent solution comprising insoluble particles.

In one embodiment of the invention, the total weight of the effervescent tablet ranges from about 500 mg to about 5000 mg, preferably, in the range of about 1000 mg to about 3000 mg, such as e.g. about 1000 mg, about 1100 mg, about 1200 mg, about 1300 mg, about 1300 mg, about 1400 mg, about 1500 mg, about 1600 mg, 1700 mg, about 1800 mg, about 1900 mg, about 2000 mg, etc.

The present effervescent tablet may be used together with other dental health products and treatment methods, such as e.g. tooth brushing, methods and preparations for the application of fluoride, salivary gland stimulation methods and preparations etc.

EXAMPLES

The present invention will now be described in more detail with reference to examples, which are not to be contemplated as restrictive or limiting to the scope of the present invention. One skilled in the art will recognize that the specific amounts of the ingredients may be adjusted respectively to arrive at a supersaturated solution having ion concentrations in the intended ranges.

Example 1

Preparation of Effervescent Tablets

The suitable amount of effervescing organic acid component and the diluent was weight and sieved and tumble mixed for approx. 5 min at 8 rpm in order to homogenize the mixture. The obtained mixture was then granulated in a fluid bed granulated. The obtained granulate was dried (air temperature 60±10° C.), keeping the temperature below 65° C. until the residual humidity was below 0-0.20%. The granulate was then cooled, sieved and tumble mixed for 5 min at 8 rpm.

The suitable amounts of the remaining constituents (effervescing base component, active ingredients, etc.) was weighted and added into the granulate and mixed for 20 minutes at 8 rpm in order to homogenize the whole mixture.

The obtained mixture was compressed to tablet using a rotary tablet press equipped with punches of a convenient size, such as e.g. 18 mm or 25 mm diameter punches. A flow chart of the process is shown in FIG. 1.

Example 2

Effervescent Tablet of 3000 mg

Effervescent tablets were prepared according to the method of described in example 1 comprising sodium hydrogen carbonate, anhydrous sodium carbonate as effervescing base component and anhydrous citric acid as effervescent agents, and sorbitol as a diluent and flavouring agent, respectively, in addition to the active ingredients. The amount of the ingredients is shown in table 1.

The specified amount of anhydrous citric acid powder and sorbitol was tumble mixed and subjected to fluid bed granulation according to the process described in example 1. After sieving and mixing of the granulate, the granulate was added to a bin comprising the remaining constituents, i.e. sodium hydrogen carbonate, anhydrous sodium carbonate, calcium chloride dihydrate, dibasic sodium phosphate, and monobasic sodium phosphate and mixed, and compressed to tablets. The theoretical weight of the tablets is 3000.000 mg.

TABLE 1

| NAMES OF INGREDIENTS | UNIT FORMULA |
|---|---|
| Sodium hydrogen carbonate | 1690.515 mg |
| Sodium carbonate anhydrous | 200.000 mg |
| Calcium chloride dihydrate | 69.135 mg |
| Sodium phosphate dibasic anhydrous | 31.120 mg |
| Sodium phosphate monobasic anhydrous | 9.230 mg |
| Citric acid anhydrous powder | 900.000 mg |
| Sorbitol | 100.000 mg |
| TOTAL | 3000.000 mg |

Example 3

Effervescent Tablet of 1200 mg

Effervescent tablets were prepared according to the method of described in example 1 comprising sodium hydrogen carbonate, anhydrous sodium carbonate as effervescing base component and anhydrous citric acid as effervescent agents, and sorbitol as a diluent and flavouring agent, respectively, and also maltodextrin as yet a diluent, in addition to the active ingredients. The amount of the ingredients is shown in table 2.

The specified amount of anhydrous citric acid powder and sorbitol was tumble mixed and subjected to fluid bed granulation according to the process described in example 1. After sieving and mixing of the granulate, the granulate was added to a bin comprising the remaining constituents, i.e. sodium hydrogen carbonate, anhydrous sodium carbonate, calcium chloride dihydrate, maltodextrin, dibasic sodium phosphate, and monobasic sodium phosphate and mixed, and compressed to tablets. The theoretical weight of the tablets is 1200.000 mg mg.

TABLE 2

| NAMES OF INGREDIENTS | UNIT FORMULA |
|---|---|
| Sodium hydrogen carbonate | 512.277 mg |
| Sodium carbonate anhydrous | 60.606 mg |
| Maltodextrin | 214.601 mg |
| Calcium chloride dihydrate | 69.135 mg |
| Sodium phosphate dibasic anhydrous | 31.120 mg |
| Sodium phosphate monobasic anhydrous | 9.230 mg |
| Citric acid anhydrous powder | 272.727 mg |
| Sorbitol | 30.303 mg |
| TOTAL | 1200.000 mg |

Example 4

Effervescent Tablet of 1100 mg

Effervescent tablets were prepared according to the method of described in example 3. The theoretical weight of the tablets is 1100.000 mg.

TABLE 3

| NAMES OF INGREDIENTS | UNIT FORMULA |
|---|---|
| Sodium hydrogen carbonate | 450.000 mg |
| Sodium carbonate anhydrous | 50.000 mg |
| Maltodextrin | 225.515 mg |
| Calcium chloride dihydrate | 69.135 mg |
| Sodium phosphate dibasic anhydrous | 31.120 mg |
| Sodium phosphate monobasic anhydrous | 9.230 mg |
| Citric acid anhydrous | 238.500 mg |
| Sorbitol | 26.500 mg |
| TOTAL | 1100.000 mg |

Example 5

Dissolution Test and pH Measurements

The dissolution characteristics of the effervescent tablets of the present invention have been tested by dropping a tablet in a bottle comprising 50 ml water and measuring the time of heavy effervesce (effervescent time) and the time for the total dissolution of the tablet. The time until no effervescence as well as the total dissolution time (the tablet was completely dissolved) were determined and are given in table 4 below.

In addition, it was determined whether the solution maintained clear. The results showed that the solution obtained remained clear for at least 2 hr.

The results showed that the dissolution of the tablets in water provided a clear solution. The solution obtained remained clear for at least 2 hr.

In addition, the pH of the obtained solution was measured in accordance with the European Pharmacopoeia 7.0, chapter 2.2.3. The results are shown in table 4.

TABLE 4

Dissolution of effervescent tablets of the invention.

| Tablet | pH of obtained solution | Effervescent time (sec) | Total dissolution time (sec) | Precipitation after 2 hr |
|---|---|---|---|---|
| 1200 mg tablet | 6.91 | 30-35 | 60 | No |
| 3000 mg tablet | 6.58 | 45-55 | 60 | No |

Example 6

Dissolution Study

In order to demonstrate that a solution is obtained in which the drug substances are completely dissolved, a dissolution study of the drug substances was performed on sample solutions, by determining the quantity of active substances dissolved in water immediately after the disintegration of the tablet, both on the solution as such and on the solution filtered through a suitable filter. A non significant difference between the average values of the filtered and unfiltered assays (see formula below) has been taken as a demonstration that the drug substances is completely dissolved. Samples were prepared by disintegrating one single unit of the finished product in 50 ml of purified water at room temperature. An aliquot of this solution is directly analyzed and another aliquot is analyzed after the filtration.

Formula:

$$\Delta\% = |U-F|/U \times 100$$

U=Average content in the unfiltered solution.
F=Average content in the filtered solution.

The result of the test shows that the tablets of the invention disintegrate well within 60 sec and in accordance with Ph. Eur 0499: N.M.T, 300 sec. The solution obtained is furthermore colourless and clear.

Formula:

$$\Delta\% = |U-F|/U \times 100$$

U=Average content in the unfiltered solution.
F=Average content in the filtered solution.

The result of the test shows that the tablets of the invention disintegrate well within 60 sec and in accordance with Ph. Eur 0499: N.M.T, 300 sec. The solution obtained is furthermore colourless and clear.

Example 7

Comparative Study

A comparative dissolution study was conducted in order to demonstrate possible differences between the composition according to the present invention (hereinafter denoted the test product) and the powder presently available on the marked (NeutraSal®, hereinafter denoted the reference product) upon disintegration in water. The products tested were the following:

Effervescent tablets according to the present invention; Batch X2KO0011 (test product)

versus

NeutraSal®, supersaturated Calcium Phosphate Rinse, dissolving powder, marketed in USA by Invado Pharmaceuticals, LLC Pomona, N.Y. (reference product).

The two medicinal products contain about the same quantity of therapeutic moiety, but in different form, i.e. an effervescent tablet vs. a dissolving powder. Before the administration, the products have to be disintegrated in water and a solution is thus obtained which are to be administered to the patients. Upon dissolution in 30 ml water, the reference product resulted in an opalescent solution comprising insoluble particles, whereas the composition according to the present invention resulted in a clear solution without any insoluble particles. In order to demonstrate that the obtained filtered\unfiltered solutions have the same concentration of the active substances, a dosage unit of both the investigated products is disintegrated under the standardized conditions (cf. the methods and results thereof described in in paragraphs 7.1 and 7.2 below). The results of the physical tests are reported in the following table 5.

TABLE 5

| TESTS | REFERENCE PRODUCT batch 122457A | TEST PRODUCT batch X2KO0011 |
|---|---|---|
| Appearance of solution | Colorless and opalescent solution with undissolved particles | Colorless and limpid solution without undissolved particles |

TABLE 5-continued

| TESTS | REFERENCE PRODUCT batch 122457A | TEST PRODUCT batch X2KO0011 |
|---|---|---|
| Disintegration time (as described in the Ph. Eur. monograph 0478) | NA | 56 |
| pH of solution | 6.9 | 6.5 |

7.1 Calcium Content in the Solutions

The test samples for the test product and the reference product were prepared as follows:

Not Filtered Solution

Three single units were weighed, and then dissolved in 90 ml of purified water. 30.0 ml of the obtained solution was withdrawn and this solution was transferred to a 250 ml beaker, then added about 100 ml of purified water, 5 ml of Sodium Hydroxide solution 40% (pH of sample 12) and 5-10 drops of Hydroxynaphtol blue solution. The obtained mixture was stirred and titrated with EDTA 0.02N.

Filtered Solution

Three single units were weighed, and then dissolve in 90 ml of purified water. The obtained solutions were then filtered (double RC filter 0.22 µm) and 30.0 ml of the filtered solution were withdrawn and transferred to a 250 ml beaker. Then about 100 ml of purified water, 5 ml of Sodium Hydroxide solution 40% (pH of sample 12) and 5-10 drops of Hydroxynaphtol blue solution were added, the mixture stirred and titrated with EDTA 0.02N.

TABLE 6

| TEST PRODUCT | | | |
|---|---|---|---|
| TEST PRODUCT | Calcium content (mg/unit) | | |
| effervescent tablets Batch: X2KO011 | Filtered - F (mg/unit) | Unfiltered - U (mg/unit) | Δ %(*) |
| Solution no. 1 | 18.49 | 18.72 | 1.3 |
| Solution no. 2 | 18.06 | 18.22 | 0.9 |
| Solution no. 3 | 17.92 | 17.92 | 0.0 |
| Average content | 18.16 | 18.29 | 0.7 |

(*)Δ % = (U − F)/U * 100
U = Content in the unfiltered solution;
F = Content in the filtered solution

TABLE 7

| REFERENCE PRODUCT | | | |
|---|---|---|---|
| REFERENCE PRODUCT | Calcium content (mg/unit) | | |
| dissolving powder Batch: 122457A | Filtered - F (mg/unit) | Unfiltered - U (mg/unit) | Δ %(*) |
| Solution no. 1 | 11.62 | 11.30 | 2.8 |
| Solution no. 2 | 11.55 | 11.44 | 1.0 |
| Solution no. 3 | 11.70 | 11.52 | 1.6 |
| Average content | 11.62 | 11.42 | 1.8 |

(*)Δ % = (U − F)/U * 100
U = Content in the unfiltered solution;
F = Content in the filtered solution

CONCLUSION

After dissolution in water, the test product, i.e. the active ingredients and the excipients, are completely dissolved. In contrast to the test product, the dissolution of the reference product resulted in an opalescent solution comprising insoluble particles. Only when the solution obtained by disintegration of the reference product was filtrated, a clear solution was obtained. Moreover, no significant difference between the Calcium assay of the filtered and unfiltered solutions were observed for the test product and the reference product, respectively.

7.2 Phosphate Content in the Solutions

The test samples for both the test product and the reference product were prepared as follows:

Not Filtered Solution

Three single unit was weighed and introduced in a 100 ml volumetric flask; the unit was then dissolved with deionised water, the obtained solution was mixed and sonicated for few minutes. The obtained mixture was brought up to volume with deionised water. 5.0 ml of the obtained solution was then transferred to a 100 ml volumetric flask and the volume again brought up to volume with deionised water (dil. 1). 5.0 ml of dil. 1 was withdrawn and transferred to a 50 ml volumetric flask, and 1.5 ml of Ascorbic acid solution (7% w/v), about 30 ml of deionised water and 1.5 ml of Molybdate reagent solution were then added. The volume was brought up to volume with deionised water, left to react for 10 minutes at RT. Then, the absorbance at 704 nm was read. It is noted that the test solution (both of the test product and the reference product) is not stable and must be read immediately after its preparation.

Filtered Solution

Three single unit were weighed and introduced in a 100 ml volumetric flask; then dissolved in deionised water, mixed and sonicated for a few minutes. The volume was thereafter brought up to volume with deionised water. An aliquot of the obtained solution was then filter (double RC filter 0.22 μm). 5.0 ml of the filtered solution was then withdrawn and transferred to a 100 ml volumetric flask, and the volume brought up to volume with deionised water (dil. 1). 5.0 ml of dil. 1 was withdrawn, transferred to a 50 ml volumetric flask, and 1.5 ml of Ascorbic acid solution (7% w/v), about 30 ml of deionised water and 1.5 ml of Molybdate reagent solution was then added. The volume was then again brought up to volume with deionised water, and left to react for 10 minutes at RT. Then, the absorbance at 704 nm was read. It is noted that the test solution (both of the test product and the reference product) is not stable and must be read immediately after its preparation.

TABLE 8

TEST PRODUCT

| TEST PRODUCT | Phosphate content (mg/unit) | | |
|---|---|---|---|
| effervescent tablets Batch: X2KO011 | Filtered - F (mg/unit) | Unfiltered - U (mg/unit) | Δ %(*) |
| Solution no. 1 | 26.0 | 24.3 | 7.0 |
| Solution no. 2 | 26.7 | 25.2 | 6.0 |
| Solution no. 3 | 26.5 | 24.8 | 6.8 |
| Average content | 26.4 | 24.8 | 6.6 |

(*)Δ % = (U − F)/U * 100
U = Content in the unfiltered solution;
F = Content in the filtered solution

TABLE 9

REFERENCE PRODUCT

| REFERENCE PRODUCT | Phosphate content (mg/unit) | | |
|---|---|---|---|
| dissolving powder Batch: 122457A | Filtered - F (mg/unit) | Unfiltered - U (mg/unit) | Δ %(*) |
| Solution no. 1 | 10.99 | 12.04 | 8.7 |
| Solution no. 2 | 11.87 | 14.14 | 16.0 |
| Solution no. 3 | 16.68 | 17.71 | 5.8 |
| Average content | 14.63 | 13.18 | 9.9 |

(*)Δ % = (U − F)/U * 100
U = Content in the unfiltered solution;
F = Content in the filtered solution

CONCLUSION

After dissolution in water, the test product, i.e. the active ingredients and the excipients, are completely dissolved. In contrast to the test product, the dissolution of the reference product resulted in an opalescent solution comprising insoluble particles. Only when the solution obtained by disintegration of the reference product was filtrated, a clear solution was obtained. Moreover, no significant difference was found between the Phosphate assay of the filtered and unfiltered solutions obtained for the test product and the reference product, respectively.

The invention claimed is:

1. An effervescent tablet comprising:
   a) a pharmaceutically effective amount of one or more sodium phosphate salts;
   b) a pharmaceutically effective amount of calcium chloride;
   c) one or more effervescing organic acid component; and
   d) one or more effervescing base component;
   wherein said tablet upon dissolution in 50 mL of water provides a supersaturated solution of calcium and phosphate ions, wherein the concentration of calcium ions provided in the obtained supersaturated solution upon dissolution of the effervescent tablet in the 50 mL of water is 2.5-16 mM, and wherein the concentration of phosphate ions provided in the obtained supersaturated solution upon dissolution of the effervescent tablet in the 50 mL of water is 1.5-10 mM,
   wherein the tablet upon dissolution in 50 mL of water results in a solution that remains clear for at least 15 minutes.

2. The effervescent tablet according to claim 1, wherein the tablet comprises a pharmaceutically effective amount of dibasic sodium phosphate and monobasic sodium phosphate.

3. The effervescent tablet according to claim 1, wherein the effervescing organic acid component is selected from the group consisting of organic mono-, di- and tricarboxylic acids, and oxyacids, salts of organic acids and salts of inorganic acids, and combinations thereof.

4. The effervescent tablet according to claim 3, wherein the effervescing organic acid component is citric acid.

5. The effervescent tablet according to claim 1, wherein the one or more effervescing base components is a carbonate salt.

6. The effervescent tablet according to claim 5, wherein the one or more effervescing bases is selected from the group consisting of sodium carbonate, magnesium carbonate, sodium hydrogen carbonate, potassium carbonate, potassium hydrogen carbonate, calcium carbonate and magnesium carbonate.

7. The effervescent tablet according to claim 6, wherein composition comprises sodium carbonate and sodium hydrogen carbonate.

8. The effervescent tablet according to claim 1, wherein the tablet upon dissolution in water results in a solution of about pH 6.5.

9. The effervescent tablet according to claim 1, wherein the tablet upon dissolution results in a solution remaining clear for at least about 2 hr.

10. The effervescent tablet according to claim 1, wherein the tablet comprises one or more additional excipients.

11. The effervescent tablet according to claim 10, wherein the additional excipient is one or more carbohydrates selected from the group consisting of polyalcohols, dextrines and saccharides.

12. The effervescent tablet according to claim 10, wherein the additional excipient is one or more polyalcohol selected from the group consisting of sorbitol, mannitol, xylitol, and inositol or the mixture thereof.

13. The effervescent tablet according to claim 10, wherein the additional excipient is one or more saccharides selected from the group consisting of glucose, fructose and sucrose, or the mixture thereof.

14. The effervescent tablet according to claim 10, wherein the excipient is a flavour and/or sweetener.

15. The effervescent tablet according to claim 10, wherein the flavour and/or sweetener is selected from the group consisting of saccharin, aspartame, and acesulfame.

16. The effervescent tablet according to claim 1, wherein the amount of calcium per tablet is in the range of about 14-24 mg.

17. The effervescent tablet according to claim 1, wherein the amount of phosphate per tablet is in the range of about 28-36 mg.

18. The effervescent tablet according to claim 1, wherein the tablet comprises a molar ratio of $NaH_2PO_4:Na_2HPO_4:CaCl_2 \times 2H_2O$ of about 1:3:6.

19. The effervescent tablet according to claim 1, comprising:
    about 69.1 mg calcium chloride dihydrate;
    about 9.2 mg monobasic sodium phosphate;
    about 31.1 mg dibasic sodium phosphate;
    about 450.0 mg sodium hydrogen carbonate;
    about 50.0 mg sodium carbonate;
    about 238.5 mg citric acid;
    about 225.5 mg maltodextrine; and
    about 26.5 mg sorbitol.

20. The effervescent tablet according to claim 1, comprising:
    about 69.1 mg calcium chloride dihydrate;
    about 9.2 mg monobasic sodium phosphate;
    about 31.1 mg dibasic sodium phosphate;
    about 512.3 mg sodium hydrogen carbonate;
    about 60.6 mg sodium carbonate;
    about 272.7 mg citric acid;
    about 214.6 mg maltodextrine; and
    about 30.3 mg sorbitol.

21. The effervescent tablet according to claim 1, comprising:
    about 69.1 mg calcium chloride dihydrate;
    about 9.2 mg monobasic sodium phosphate;
    about 31.1 mg dibasic sodium phosphate;
    about 1690.5 mg sodium hydrogen carbonate;
    about 200.0 mg sodium carbonate;
    about 900.0 mg citric acid; and
    about 100.0 mg sorbitol.

22. A process for the preparation of effervescent tablets according to claim 1, comprising the steps of:
    a) mixing the one or more effervescing organic acid components and a diluent to provide a mixture;
    b) subjecting the mixture of step a) to granulation to provide a granulate;
    c) drying the granulate obtained in step b) to provide a dried granulate;
    d) mixing the dried granulate of step c) with the one or more effervescing base component, a pharmaceutically effective amount of one or more phosphate salt(s), a pharmaceutically effective amount of a calcium salt, and optionally one or more pharmaceutically acceptable excipients; and
    e) compressing the mixture of step d) to form tablets.

23. A process for preventing or treating inflammatory processes of the soft tissues of the mouth, throat and oral cavity, comprising the steps of diluting an effervescent tablet according to claim 1 in a suitable amount of water in order to dissolve the tablet, and administering the obtained solution to the patient as an oral rinse.

24. The effervescent tablet according to claim 1, wherein the tablet upon dissolution results in a solution remaining clear for at least about 30 minutes.

25. The effervescent tablet according to claim 1, wherein the tablet upon dissolution results in a solution remaining clear for at least about 60 minutes.

* * * * *